United States Patent
Umada et al.

(10) Patent No.: US 6,600,079 B2
(45) Date of Patent: Jul. 29, 2003

(54) PROCESS FOR PRODUCTION OF 5-ARYLPENTANOLS

(75) Inventors: Akira Umada, Wakayama (JP); Shigeyoshi Tanaka, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/254,661

(22) Filed: Sep. 26, 2002

(65) Prior Publication Data

US 2003/0060667 A1 Mar. 27, 2003

(30) Foreign Application Priority Data

Sep. 27, 2001 (JP) ........................ 2001-296249

(51) Int. Cl.$^7$ ............................... C07C 27/00
(52) U.S. Cl. ....................................... 568/814
(58) Field of Search ......................... 568/814

(56) References Cited

U.S. PATENT DOCUMENTS 5,162,551 A * 11/1992 Broekhof
5,219,836 A * 6/1993 Watkins
5,907,048 A * 5/1999 Nishioka

FOREIGN PATENT DOCUMENTS

CH 655 932 2/1983

OTHER PUBLICATIONS

Robert H. Baker, et al., "The Cleavage of Benzyl Ethers with Hydrogen," *Journal of the American Chemical Society*, vol. 70, No. 4, Apr. 1948, pp. 1490–1492.

* cited by examiner

*Primary Examiner*—Michael L. Shippen
(74) *Attorney, Agent, or Firm*—Oblon, Spivak, McClelland, Maier & Neustadt, P.C.

(57) ABSTRACT

A process for producing a 5-arylpentanol of formula (2):

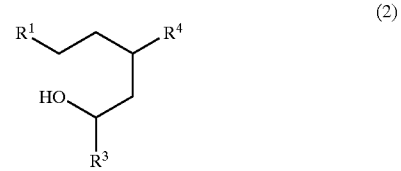

wherein $R^1$ represents an aryl group which may be substituted with one or two or more of an alkyl or alkoxy group and has 6 to 12 carbon atoms in total, $R^3$ represents a hydrogen atom, or an alkyl or alkenyl group of 1 to 6 carbon atoms, and $R^4$ represents $R^2$ defined below when $R^2$ is a monovalent group or represents $R^2H$ when $R^2$ is a divalent group, which comprises effecting hydrogenolysis of a pyran compound of formula (1):

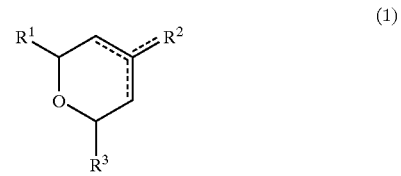

wherein, $R^1$ and $R^3$ are as defined above, $R^2$ represents a hydrogen atom, an alkyl or alkenyl group of 1 to 6 carbon atoms, or an alkylidene or alkenylidene group of 1 to 6 carbon atoms, and a dotted line represents a possible bond and any one of the three bonds represented by dotted lines and solid lines is a double bond, in the presence of one or more catalysts selected from (a) a catalyst carrying two or more elements selected from noble metals in Group VIII in the periodic table and (b) an acid type palladium-supporting catalyst. 5-arylpentanols can be prepared in a high yield with low production of hydrocarbons without causing a problem with regard to corrosion of process equipment.

10 Claims, No Drawings

PROCESS FOR PRODUCTION OF 5-ARYLPENTANOLS

BACKGROUND OF THE INVENTION

1. Field of the Invention

The present invention relates to a process for producing 5-arylpentanols that are useful as synthetic intermediates of perfume, medicaments, agricultural chemicals and the like from pyran compounds.

2. Description of the Prior Art

Hitherto, there have been known, as a method for obtaining 5-arylpentanols, a method for producing a 5-aryl-3-methylpentanol by hydrogenolysis of 2-phenyl-4-methylenepyran using a metal catalyst such as palladium and an acid substance such as an inorganic proton acid or acidic diatomaceous earth (Switzerland Patent No.655932) and a method for producing 5-phenylpentanol by hydrogenolysis of 2-phenyltetrahydropyran in an acetic acid solution containing perchloric acid in the presence of a palladium catalyst (J. Am. Chem. Soc., 70, 1490–1492 (1948)).

On the other hand, there is no prior art for effectively producing a 5-arylpentanol through hydrogenolysis of a pyran compound in the absence of an acidic substance. This is because the rate of hydrogenolysis reaction is significantly decreased if an acidic substance is not used.

However, a process using an acidic substance is not industrially favorable because a large amount of by-products is produced, the yield of a 5-arylpentanol is not necessarily high, there is a problem with regard to corrosion of process equipment owing to the use of the acidic substance, and waste is increased, thereby increasing an environmental load.

SUMMARY OF THE INVENTION

An object of the present invention is to provide a process for producing a 5-arylpentanol in a high yield with little amount of by-products.

Another object of the invention is to provide a process for producing a 5-arylpentanol which does not bring about a problem with regard to corrosion of process equipment and is industrially satisfactory.

The present inventors have found, after intensive researches, that the aimed product can be obtained in a high yield and industrially satisfactorily while suppressing production of by-products without using a special corrosion-resistant equipment by effecting hydrogenolysis in the presence of a supported catalyst of two or more elements selected from the noble metals in Group VIII in the periodic table and/or an acidic-type palladium-supporting catalyst, and have completed the invention.

There is thus provided a process for producing a 5-arylpentanol of formula (2):

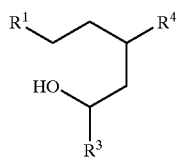

(2)

wherein,
$R^1$ represents an aryl group which may be substituted with one or two or more of an alkyl or alkoxy group and has 6 to 12 carbon atoms in total, $R^3$ represents a hydrogen atom, or an alkyl or alkenyl group of 1 to 6 carbon atoms, and $R^4$ represents $R^2$ defined below when $R^2$ is a monovalent group or represents $R^2H$ when $R^2$ is a divalent group, which comprises effecting hydrogenolysis of a pyran compound of formula (1):

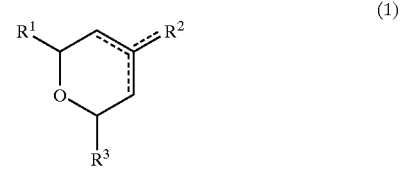

(1)

wherein,
$R^1$ and $R^3$ are as defined above,
$R^2$ represents a hydrogen atom, an alkyl or alkenyl group of 1 to 6 carbon atoms, or an alkylidene or alkenylidene group of 1 to 6 carbon atoms, and a dotted line ( - - - ) represents a possible bond and any one of the three bonds represented by dotted lines and solid lines is a double bond, in the presence of one or more catalysts selected from (a) a catalyst carrying two or more elements selected from noble metals in Group VIII in the periodic table and (b) an acid type palladium-supporting catalyst.

DESCRIPTION OF THE PREFERRED EMBODIMENTS

In the pyran compounds of the formula (1), $R^1$ is preferably an aryl group having in total 6 to 12 carbon atoms which may be substituted with one or two or more of alkyl or alkoxy groups each having 1 to 6 carbon atoms. The aryl group includes phenyl group and naphthyl group, and is preferably phenyl group. $R^1$ is particularly preferably phenyl, or o-, m- or p-tolyl, and most preferably phenyl.

$R^2$ is preferably a hydrogen atom or an alkyl or alkylidene group having 1 to 6 carbon atoms, more preferably a hydrogen atom, methyl group or methylene group, and most preferably a hydrogen atom or methyl group.

$R^3$ is preferably a hydrogen atom or an alkyl group having 1 to 6 carbon atoms, and particularly preferably a hydrogen atom or methyl group.

Examples of the pyran compounds include 6-phenyl-4-methyl-5,6-dihydro-2H-pyran, 6-phenyl-2,4-dimethyl-5,6-dihydro-2H-pyran, 6-p-tolyl-4-methyl-5, 6-dihydro-2H-pyran, 2-phenyl-4-methylenetetrahydro-2H-pyran, and 2-phenyl-4-methyl-5,6-dihydro-2H-pyran.

One of the preferred embodiments of the present invention is a process for producing a 5-arylpentanol of formula (2a):

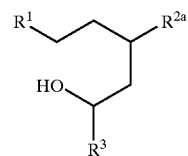

(2a)

wherein,
$R^1$ represents an aryl group which may be substituted with one or two or more of an alkyl or alkoxy group and has 6 to 12 carbon atoms in total, and $R^{2a}$ and $R^3$ may be the same or different and represent a hydrogen atom, or an alkyl or alkenyl group of 1 to 6 carbon atoms, which comprises effecting hydrogenolysis of a 5,6-dihydro-2H-pyran compound of formula (1a):

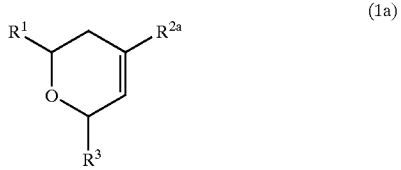

wherein, $R^1$, $R^{2a}$ and $R^3$ are as defined above, in the presence of one or more catalysts selected from (a) a catalyst carrying two or more elements selected from noble metals in Group VIII in the periodic table and (b) an acid type palladium-supporting catalyst.

In formula (1a), preferred groups as $R^1$ and $R^3$ are the same as those described for $R^1$ and $R^3$ in formula (1). $R^{2a}$ is preferably a hydrogen atom or an alkyl group having 1 to 6 carbon atoms, and more preferably a hydrogen atom or methyl group.

In the catalyst carrying two or more elements selected from noble metals in Group VIII in the periodic table, the noble metals include palladium, platinum, rhodium and ruthenium. Carriers for the noble metals include carbon, alumina, silica gel, barium sulfate, zeolite and calcium carbonate. The catalyst may be two or more noble metals supported on one kind of carrier, or a mixture of two or more kinds of carriers each carrying one kind of noble metal. The amount of each noble metal supported on a carrier is preferably 0.1 to 10% by weight, and more preferably 0.2 to 8% by weight of the catalyst. Total amount of two or more noble metals supported on carrier(s) is preferably 1 to 20% by weight, more preferably 2 to 10% by weight of the catalyst. These catalysts can be obtained by a well known method, for example by an impregnation supporting method ("Catalyst Preparation Chemistry" edited by Atsumu Ozaki, published by Kodansha) in which a carrier is impregnated with a metal and the resulting carrier is reduced with hydrogen at a higher temperature. Alternatively, commercial products may be used as they are. Examples of such commercial products include Palladium-Platinum-Carbon powder, Palladium-Carbon Powder, Platinum-Carbon Powder, and Ruthenium-Carbon Powder each manufactured by N. E. Chemcat Corporation.

The acid type palladium-supporting catalyst used in the present invention means such a solid palladium catalyst in which palladium is supported on at least one carrier selected from alumina, silica gel, barium sulfate, zeolite and calcium carbonate and which shows a pH of less than 7, preferably 2 to 6, particularly preferably 3 to 5.5 when it is dispersed in water. For example, when 4 g of the catalyst is dispersed in 30 g of pure water for 5 minutes, the resulting water has a pH of less than 7, preferably 2 to 6, particularly preferably 3 to 5.5. If the pH of the catalyst is not less than 7, production rate of a 5-arylpentanol significantly decreases. The amount of palladium in the catalyst is preferably 0.5 to 10% by weight, particularly 2 to 10% by weight of the catalyst. Such catalysts can be obtained by a well known method, for example by impregnating a carrier with a metal according to an impregnation supporting method ("Catalyst Preparation Chemistry" edited by Atsumu Ozaki, published by Kodansha), and reducing the resulting carrier with hydrogen at a higher temperature. Alternatively, commercially available catalysts may be used. For example, among commercially available palladium-carbon powders manufactured by N. E. Chemcat Corporation, those having a pH in the above-mentioned range may be used.

The amount of the catalyst to be used in the invention is usually in a range of 0.01 to 5% by weight, preferably in a range of 0.05 to 5% by weight based on the pyran compounds although it varies depending on the amount of the metals contained in the catalyst; use of too little amount of the catalyst results in a low reaction rate while use of too much amount of the catalyst results in much production of by-products such as hydrocarbons and excessive reaction products wherein the benzene ring of a 5-aryl pentanol is hydrogenated and thus is not economical. Particularly, when the catalyst carrying two or more elements selected from the noble metals in Group VIII in the periodic table is used, it is used in an amount of 0.01 to 2% by weight, preferably 0.05 to 1% by weight based on the pyran compounds. Either of the two kinds of the catalysts can be re-used.

The reaction in the present invention may be carried out using a solvent. Alcohol solvents are preferred as the solvent and examples thereof include methanol, ethanol, 1-propanol and 2-propanl. These solvents may be used alone or as a mixture of two or more thereof.

Use of too much solvent results in decrease in the production of 5-arylpentanols and besides is not economical. Thus, the amount of the solvent used in the reaction is preferably not more than 60% by weight based on the pyran compound. Alternatively, solvents may not be used.

The reaction may be conducted at a constant temperature. However, it is preferable to conduct the reaction at a relatively lower temperature in the early stage of reaction and then increase the temperature at the later stage of reaction in order to suppress production of by-products and to increase the production rate of 5-arylpentanols.

In the present invention, the later stage of reaction begins preferably from the time when conversion of the raw material, pyran compounds, reaches about 60 to 95%, particularly about 80 to 90%, which time usually corresponds to about 1 to 4 hours after commencement of the reaction although such time varies depending on the reaction temperature and the like. The reaction temperature in the later stage of reaction is preferably higher than that in the early stage of reaction. At the end of the early stage of reaction, the temperature is increased with time at a rate preferably in a range of from 3 to 20° C. per minute.

Hydrogenolysis of the pyran compounds is effected at about 30 to 300° C., preferably at about 40 to 200° C. In order to sufficiently react the raw material, pyran compounds, and to suppress production of by-products, the reaction is desirably conducted at about 40 to 100° C., preferably 50 to 80° C. at the early stage of reaction. Thereafter, in the later stage of reaction, the reaction temperature is increased to a temperature higher than that in the early stage of reaction by about 30 to 260° C. to enhance the production rate of 5-arylpentanols. In order to suppress excessive reaction of the resulting 5-arylpentanols, it is desirable to increase the temperature in the later stage of reaction to a temperature higher than that in the early stage of reaction by about 30 to 160° C., more preferably by about 40 to 130° C. The reaction temperature in the later stage of reaction is preferably in a range of from about 120 to 180° C.

Hydrogen pressure during reaction is in a range of 0.2 to 10 MPaG, preferably 0.5 to 5 MPaG; too lower hydrogen pressure results in insufficient production rate of 5-arylpentanols.

The invention will be hereinafter explained more in detail by way of the following examples which are not intended to restrict the invention. In the examples, percentages are based on weight.

EXAMPLE 1

In an autoclave made of SUS304 were charged 110 g of 6-phenyl-4-methyl-5,6-dihydro-2H-pyran, 44 g of 2-propanol and 0.55 g of 4.5% Pd-0.5% Pt-carbon powder water-containing product (manufactured by N. E. Chemcat Corporation). After pressurization to 2 MPa with hydrogen, the mixture was subjected to reaction at 80° C. for 7 hours. After completion of the reaction, the reaction mixture was filtered to remove the catalyst and was analyzed by gas chromatography. As the result, the yield of 5-phenyl-3-methylpentanol was 83.1%. The reaction product contained 3.6% of hydrocarbons and 0.8% of excessive reaction products.

EXAMPLE 2

In an autoclave made of SUS304 were charged 110 g of 6-phenyl-4-methyl-5,6-dihydro-2H-pyran, 44 g of 2-propanol, 0.50 g of 5% Pd-carbon powder water-containing product (acid-type catalyst, pH 3.9, manufactured by N. E. Chemcat Corporation) and 0.06 g of 5% Rh-carbon powder water-containing product (manufactured by N. E. Chemcat Corporation). After pressurization to 2 MPa with hydrogen, the mixture was subjected to reaction at 80° C. for 7 hours. After completion of the reaction, the reaction mixture was filtered to remove the catalysts and was analyzed by gas chromatography. As the result, the yield of 5-phenyl-3-methylpentanol was 80.7%. The reaction product contained 1.4% of hydrocarbons and 0.8% of excessive reaction products.

EXAMPLE 3

In an autoclave made of SUS304 were charged 110 g of 6-phenyl-4-methyl-5,6-dihydro-2H-pyran, 44 g of 2-propanol and 0.22 g of 4.5% Pd-0.5% Pt-carbon powder water-containing product (manufactured by N. E. Chemcat Corporation). After pressurization to 2 MPa with hydrogen, the mixture was subjected to reaction at 60° C. for 2 hours. It was confirmed by gas chromatography that the conversion of 6-phenyl-4-methyl-5,6-dihydro-2H-pyran was 88%. Thereafter, the reaction temperature was raised to 150° C. in 19 minutes and reaction was conducted for additional 5 hours. After completion of the reaction, the reaction mixture was filtered to remove the catalyst and was analyzed by gas chromatography. As the result, the yield of 5-phenyl-3-methylpentanol was 93.4%. The reaction product contained 1.3% of hydrocarbons and 2.1% of excessive reaction products.

EXAMPLE 4

In an autoclave made of SUS304 were charged 110 g of a mixture of 6-phenyl-4-methyl-5,6-dihydro-2H-pyran, 2-phenyl-4-methyl-5,6-dihydro-2H-pyran and 2-phenyl-4-methylenetetrahydro-2H-pyran (component ratio 53:46:1 according to gas chromatography), 44 g of 2-propanol and 0.22 g of 4.5% Pd-0.5% Pt-carbon powder water-containing product (manufactured by N. E. Chemcat Corporation). After pressurization to 2 MPa with hydrogen, the mixture was subjected to reaction at 60° C. for 2 hours. It was confirmed by gas chromatography that the conversion of the raw material, pyran compounds, was 88%. Thereafter, the reaction temperature was raised to 150° C. in 19 minutes and reaction was conducted for additional 5 hours. After completion of the reaction, the reaction mixture was filtered to remove the catalyst and was analyzed by gas chromatography. As the result, the yield of 5-phenyl-3-methylpentanol was 93.0%. The reaction product contained 1.8% of hydrocarbons and 2.1% of excessive reaction products.

EXAMPLE 5

In an autoclave made of SUS304 were charged 150 g of 6-phenyl-4-methyl-5,6-dihydro-2H-pyran and 0.30 g of 4.5% Pd-0.5% Pt-carbon powder water-containing product (manufactured by N. E. Chemcat Corporation). After pressurization to 2 MPa with hydrogen, the mixture was subjected to reaction at 60° C. for 2 hours. It was confirmed by gas chromatography that the conversion of 6-phenyl-4-methyl-5,6-dihydro-2H-pyran was 84%. Thereafter, the reaction temperature was raised to 150° C. in 18 minutes and reaction was conducted for additional 5 hours. After completion of the reaction, the reaction mixture was filtered to remove the catalyst and was analyzed by gas chromatography. As the result, the yield of 5-phenyl-3-methylpentanol was 89.8%. The reaction product contained 0.7% of hydrocarbons and 1.9% of excessive reaction products.

EXAMPLE 6

In an autoclave made of SUS304 were charged 100 g of 6-phenyl-4-methyl-5,6-dihydro-2H-pyran, 50 g of 2-propanol and 1.0 g of 5% Pd-carbon powder water-containing product (acid type catalyst, pH 3.9, manufactured by N. E. Chemcat Corporation). After pressurization to 2 MPa with hydrogen, the mixture was subjected to reaction at 150° C. for 8 hours. After completion of the reaction, the reaction mixture was filtered to remove the catalyst and was analyzed by gas chromatography. As the result, the yield of 5-phenyl-3-methylpentanol was 87.6%. The reaction product contained 4.1% of hydrocarbons and 6.4% of excessive reaction products.

EXAMPLE 7

In an autoclave made of SUS304 were charged 110 g of 6-phenyl-4-methyl-5,6-dihydro-2H-pyran, 44 g of 2-propanol and 1.1 g of 5% Pd-carbon powder water-containing product (acid type catalyst, pH 4.1, manufactured by N. E. Chemcat Corporation). After pressurization to 2 MPa with hydrogen, the mixture was subjected to reaction at 80° C. for 1 hour. It was confirmed by gas chromatography that the conversion of 6-phenyl-4-methyl-5,6-dihydro-2H-pyran was 97%. Thereafter, the reaction temperature was raised to 150° C. in 14 minutes and reaction was conducted for additional 3 hours. After completion of the reaction, the reaction mixture was filtered to remove the catalyst and was analyzed by gas chromatography. As the result, the yield of 5-phenyl-3-methylpentanol was 92.0%. The reaction product contained 1.9% of hydrocarbons and 4.1% of excessive reaction products.

EXAMPLE 8

In an autoclave made of SUS304 were charged 100 g of 6-phenyl-4-methyl-5,6-dihydro-2H-pyran, 50 g of 2-propanol and 1.0 g of 5% Pd-carbon powder water-containing product (acid type catalyst, pH 3.9, manufactured by N. E. Chemcat Corporation). After pressurization to 2 MPa with hydrogen, the mixture was subjected to reaction at 60° C. for 2 hours. It was confirmed by gas chromatography that the conversion of 6-phenyl-4-methyl-5,6-dihydro-2H-pyran was 89%. Thereafter, the reaction temperature was raised to 150° C. in 20 minutes and reaction was conducted for additional 3 hours. After completion of the reaction, the reaction mixture was filtered to remove the catalyst and was analyzed by gas chromatography. As the result, the yield of 5-phenyl-3-methylpentanol was 93.1%. The reaction product contained 0.8% of hydrocarbons and 3.8% of excessive reaction products.

COMPARATIVE EXAMPLE 1

In an autoclave made of SUS304 were charged 10 g of 6-phenyl-4-methyl-5,6-dihydro-2H-pyran, 44 g of 2-propanol and 0.22 g of 5% Pd-carbon powder water-containing product (pH 8.6, manufactured by N. E. Chemcat Corporation). After pressurization to 2 MPa with hydrogen, the mixture was subjected to reaction at 60° C. for 2 hours. It was confirmed by gas chromatography that the conversion of 6-phenyl-4-methyl-5,6-dihydro-2H-pyran was 83%. Thereafter, the reaction temperature was raised to 150° C. in 20 minutes and reaction was conducted for additional 5 hours. After completion of the reaction, the reaction mixture was filtered to remove the catalyst and was analyzed by gas chromatography. As the result, the yield of 5-phenyl-3-methylpentanol was 3.5%. The reaction product contained 0.5% of hydrocarbons and 0.1% of excessive reaction products.

COMPARATIVE EXAMPLE 2

In an autoclave made of SUS304 were charged 100 g of 6-phenyl-4-methyl-5,6-dihydro-2H-pyran, 50 g of 2-propanol and 1.0 g of 5% Pd-carbon powder water-containing product (pH 8.6, manufactured by N. E. Chemcat Corporation). After pressurization to 2 MPa with hydrogen, the mixture was subjected to reaction at 80° C. for 2 hours. Thereafter, the reaction temperature was raised to 180° C. and reaction was conducted for additional 6 hours. After completion of the reaction, the reaction mixture was filtered to remove the catalyst and was analyzed by gas chromatography. As the result, the yield of 5-phenyl-3-methylpentanol was 21.7%. The reaction product contained 1.8% of hydrocarbons and 1.5% of excessive reaction products.

COMPARATIVE EXAMPLE 3

In an autoclave made of SUS304 were charged 100 g of 6-phenyl-4-methyl-5,6-dihydro-2H-pyran, 50 g of 2-propanol, 1.0 g of 5% Pd-carbon powder water-containing product (pH 8.6, manufactured by N. E. Chemcat Corporation) and 12.0 g of acetic acid. After pressurization to 2 MPa with hydrogen, the mixture was subjected to reaction at 80° C. for 1 hour. Thereafter, the reaction temperature was raised to 150° C. and reaction was conducted for additional 3 hours. After completion of the reaction, the reaction mixture was filtered to remove the catalyst and was analyzed by gas chromatography. As the result, the yield of 5-phenyl-3-methylpentanol was 80.4%. The reaction product contained 10.7% of hydrocarbons and 6.5% of excessive reaction products. Black spots that are considered to be due to corrosion were found on the inner wall of the autoclave made of SUS304.

According to the present invention, 5-arylpentanol can be prepared in a high yield while suppressing production of hydrocarbons and without causing a problem with regard to corrosion of process equipment.

What is claimed is:

1. A process for producing a 5-arylpentanol of formula (2):

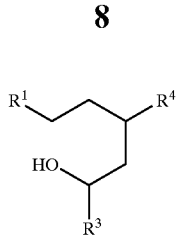

wherein,
$R^1$ represents an aryl group which may be substituted with one or two or more of an alkyl or alkoxy group and has 6 to 12 carbon atoms in total,
$R^3$ represents a hydrogen atom, or an alkyl or alkenyl group of 1 to 6 carbon atoms, and
$R^4$ represents $R^2$ defined below when $R^2$ is a monovalent group or represents $R^2H$ when $R^2$ is a divalent group,
which comprises effecting hydrogenolysis of a pyran compound of formula (1):

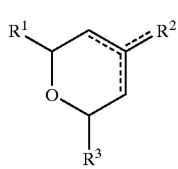

wherein,
$R^1$ and $R^3$ are as defined above,
$R^2$ represents a hydrogen atom, an alkyl or alkenyl group of 1 to 6 carbon atoms, or an alkylidene or alkenylidene group of 1 to 6 carbon atoms, and
a dotted line represents a possible bond and any one of the three bonds represented by dotted lines and solid lines is a double bond, in the presence of one or more catalysts selected from (a) a catalyst carrying two or more elements selected from noble metals in Group VIII in the periodic table and (b) an acid type palladium-supporting catalyst.

2. The process according to claim 1, wherein the reaction in the later stage of reaction is conducted at a temperature higher than that in the early stage of reaction.

3. The process according to claim 2, wherein the reaction temperature in the early stage of reaction is in a range of from 40 to 100° C., and the reaction in the later stage of reaction is conducted at a temperature higher than that in the early stage of reaction by 30 to 160° C.

4. The process according to claim 2, wherein the later stage of reaction begins from the time when the conversion of the raw material, pyran compounds, reaches 80 to 90%.

5. The process according to claim 3, wherein the later stage of reaction begins from the time when the conversion of the raw material, pyran compounds, reaches 80 to 90%.

6. The process according to claim 1, wherein the catalyst carrying two or more elements selected from noble metals in Group VIII in the periodic table is a catalyst carrying palladium and platinum.

7. The process according to claim 2, wherein the catalyst carrying two or more elements selected from noble metals in Group VIII in the periodic table is a catalyst carrying palladium and platinum.

8. The process according to claim 1, wherein the acid type palladium-supporting catalyst is such a catalyst that shows a pH in a range of from 2 to 6 when it is dispersed in water.

9. The process according to claim 2, wherein the acid type palladium-supporting catalyst is such a catalyst that shows a pH in a range of from 2 to 6 when it is dispersed in water.

10. A process for producing a 5-arylpentanol of formula (2a):

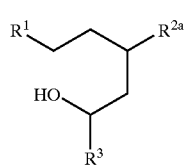

(2a)

wherein, $R^1$ represents an aryl group which may be substituted with one or two or more of an alkyl or alkoxy group and has 6 to 12 carbon atoms in total, and $R^{2a}$ and $R^3$ may be the same or different and represent a hydrogen atom, or an alkyl or alkenyl group of 1 to 6 carbon atoms, which comprises effecting hydrogenolysis of a 5,6-dihydro-2H-pyran compound of formula (1a):

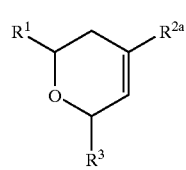

(1a)

wherein, $R^1$, $R^{2a}$ and $R^3$ are as defined above, in the presence of one or more catalysts selected from (a) a catalyst carrying two or more elements selected from noble metals in Group VIII in the periodic table and (b) an acid type palladium-supporting catalyst.

* * * * *

UNITED STATES PATENT AND TRADEMARK OFFICE
CERTIFICATE OF CORRECTION

PATENT NO.     : 6,600,079 B2
DATED          : July 29, 2003
INVENTOR(S)    : Umada et al.

It is certified that error appears in the above-identified patent and that said Letters Patent is hereby corrected as shown below:

Title page,
Item [30], Foreign Application Priority Data, should read:
-- [30] Foreign Application Priority Data
Sep. 27, 2001 (JP) ………………………….. 2001-296249
Jun. 11, 2002 (JP) ………………………….. 2002-169630 --

Signed and Sealed this

Eleventh Day of November, 2003

JAMES E. ROGAN
*Director of the United States Patent and Trademark Office*